Figure 1:
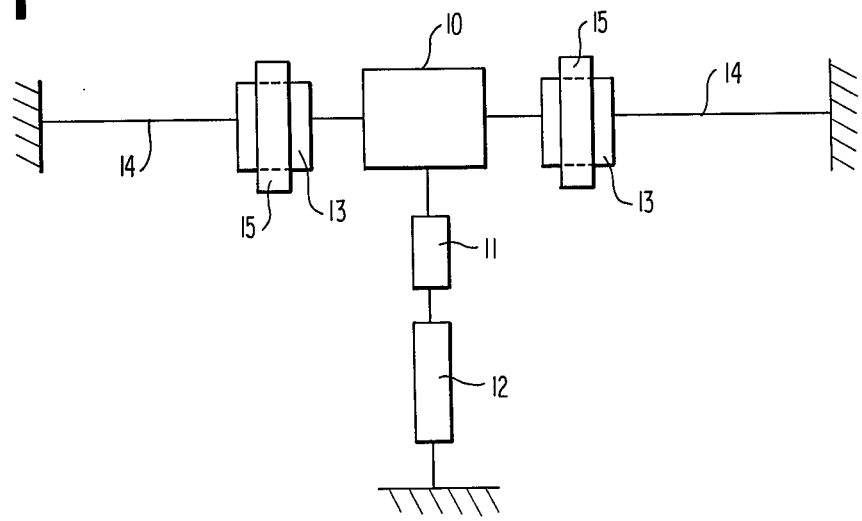

United States Patent [19]

Hornig et al.

[11] 4,196,786
[45] Apr. 8, 1980

[54] INSTALLATION FOR VIBRATION DAMPING OF A DRIVE AXLE, ESPECIALLY OF A REAR AXLE OF MOTOR VEHICLES

[75] Inventors: Rudolf Hörnig, Esslingen; Bruno Beeskow, Bietigheim; Günter Wörner, Rommelshausen, all of Fed. Rep. of Germany

[73] Assignee: Daimler-Benz Aktiengesellschaft, Fed. Rep. of Germany

[21] Appl. No.: 896,057

[22] Filed: Apr. 13, 1978

[30] Foreign Application Priority Data

Apr. 14, 1977 [DE] Fed. Rep. of Germany ....... 2716485

[51] Int. Cl.² ............................................. B60K 23/04
[52] U.S. Cl. ....................................... 180/71; 180/75; 188/1 B
[58] Field of Search ............................ 180/75, 71, 70 R; 308/74; 188/1 B; 248/358 R, 316 C, 15, 74 R, 74 B

[56] References Cited

U.S. PATENT DOCUMENTS

| 1,656,125 | 1/1928 | Neuenfelt | 308/74 |
| 3,504,573 | 4/1970 | Yoshida | 180/70 P X |
| 3,606,218 | 9/1971 | Enlund et al. | 248/74 B |
| 3,931,863 | 1/1976 | Sugiyama et al. | 180/71 |

Primary Examiner—Richard A. Bertsch
Assistant Examiner—Michael Mar
Attorney, Agent, or Firm—Craig and Antonelli

[57] ABSTRACT

An installation for damping vibrations of a drive axle, especially of a rear axle, of motor vehicles, in which the driving pinion of the differential gear which meshingly engages with the spur bevel gear, is driven by way of a universal joint shaft and in which the output from the differential gear onto the axle half-shafts takes place by way of one synchronizing joint each; for purposes of changing the resonant frequency of the system, additional annular parts constructed of shell-shape are clamped onto that part of the synchronizing joint which is connected with the output of the differential gear.

5 Claims, 2 Drawing Figures

U.S. Patent  Apr. 8, 1980  4,196,786

INSTALLATION FOR VIBRATION DAMPING OF A DRIVE AXLE, ESPECIALLY OF A REAR AXLE OF MOTOR VEHICLES

The present invention relates to an installation for damping vibrations of a drive axle, especially of a rear axle, of motor vehicles, in which the driving pinion of the differential gear which engages with the axle drive bevel wheel or spur bevel gear, is driven from a universal joint shaft and in which the output from the differential gear takes place onto the axle half-shafts by way of one synchronizing joint each.

With drive axles of the type described above, a torsional vibration excitation occurs frequently as a result of the tooth engagement pulse between the driving pinion and the spur bevel gear or axle-drive bevel wheel of the differential gear, which sets the torsional vibrational system of the drive connection into vibrations. Under certain circumstances, resonances occur within certain rotational speed ranges so that the vibrational deflections can build-up undesirably. A proposal of applicants which has equal standing with the present invention relates to the arrangement of vibration dampers in such a vibrational system. However, it has now been discovered that under certain circumstances also the subsequent installation of an arrangement for the vibration damping becomes necessary. For that purpose the solution of the vibration damper proposed by applicants which in principle is good is hardly suitable since a considerable assembly work is connected therewith so that such a subsequent installation becomes very expensive.

The present invention is therefore concerned with the task to provide an installation for damping vibrations which can be installed subsequently without great assembly costs and which also dampens the resonant amplitudes or so far displaces the natural frequency by a change of the synchronizing joint masses that a resonance can no longer occur. The underlying problems are solved according to the present invention in that for purposes of changing the resonant frequency, additional annular parts of shell-shape are clamped onto the joint part connected with the output of the differential gear.

One is able to so change the vibrating mass of the synchronizing joints by the proposal according to the present invention that a resonance no longer occur and as a result thereof, the entire vibrational system is effectively dampened. The installation of the device proposed herein is astonishingly simple and requires, for example, no disassembly of the axle itself. Consequently, installation and assembly costs are very small and also the parts additionally required therefor can be manufactured in a simple and easy manner.

The present invention contemplates preferably a construction which involves two identical half-shells that are secured to one another at their two ends and whose inner surfaces within the area of their ends serve for the secure abutment at the joint part whereas the sector disposed therebetween is provided with an abutment or contact layer of rubber or technically equivalent material. Of course, such an arrangement may also be assembled within the scope of the present invention of more than two, for example, of three shells, however, the assembly becomes somewhat more complicated as a result thereof. It is important that the shells have a completely satisfactory abutment at the joint part itself and that the rubber surfaces exhibit a sufficient contact pressure so that they achieve at the joint part a type of adhesive or gluing action, so to speak of. The additional ring mounted in this manner cannot displace in the axial direction with respect to the joint nor rotate with respect thereto.

Accordingly, it is an object of the present invention to provide an installation for the vibration damping of a drive axle, especially of a rear axle, of motor vehicles, which avoids by simple means the aforementioned shortcomings and drawbacks encountered in the prior art.

Another object of the present invention resides in a drive axle for motor vehicles, which effectively precludes the build-up of torsional vibrations in the drive connection by extremely simple means.

A further object of the present invention resides in a drive-axle, especially a rear axle for motor vehicles, in which the means for damping the vibrations can be readily installed subsequently into an existing motor vehicle.

Still another object of the present invention resides in an installation for damping vibrations which can be installed also subsequently without great assembly costs, yet effectively dampens resonant amplitudes or displaces the natural frequency by changing the synchronizing joint masses to such an extent that a resonance no longer occurs.

A further object of the present invention resides in an installation of the type described above which is surprisingly simple and requires no disassembly whatsoever of the axle itself and which involves only parts that can be readily manufactured in a simple, inexpensive manner.

Figure 2:
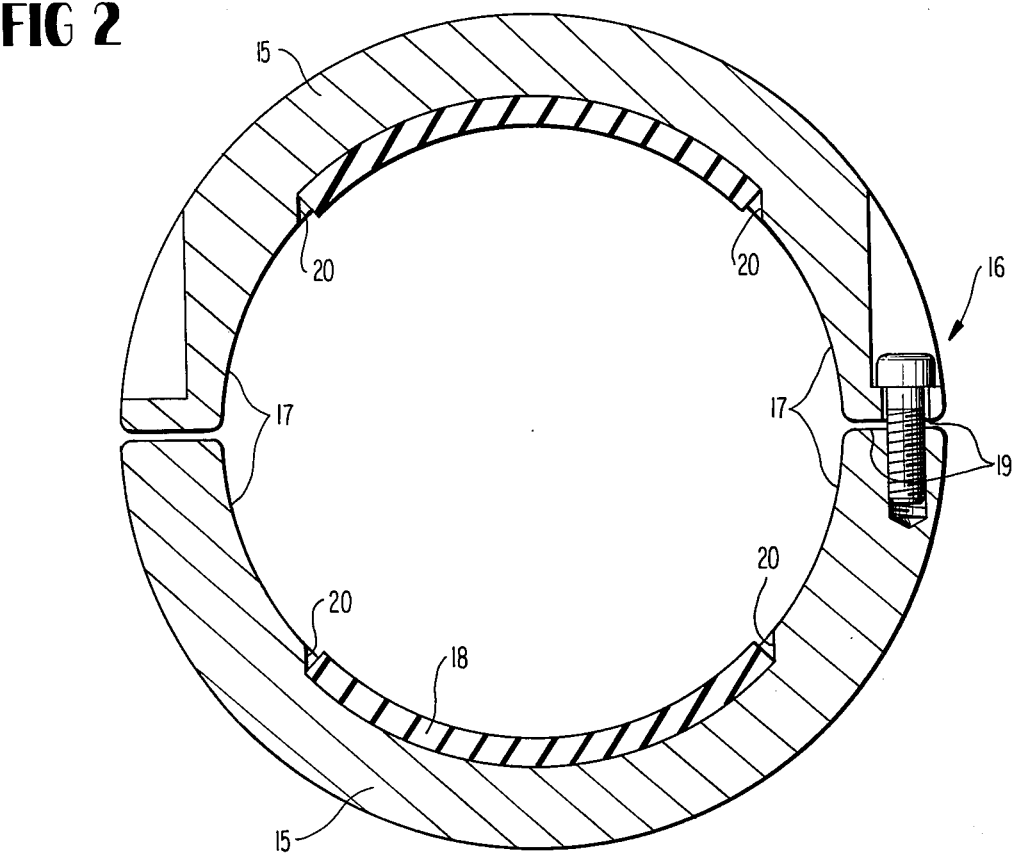

These and other objects, features and advantages of the present invention will become more apparent from the following description when taken in connection with the accompanying drawing which shows, for purposes of illustration only, one embodiment in accordance with the present invention, and wherein:

FIG. 1 is a schematic view of the vibrational system of the arrangement of the present invention; and FIG. 2 is a cross-sectional view through the additional ring consisting of two half-shells in accordance with the present invention.

Referring now to the drawing wherein like reference numerals are used throughout the two views to designate like parts, according to FIG. 1, the axle drive bevel wheel or spur bevel gear in the differential gear 10 is in meshing engagement in a conventional manner with its driving pinion 11 which is driven by way of a cardan shaft 12. Two synchronizing joints 13 are arranged at the two outputs of the differential gear 10 which are constructed as sliding joints and which drive the half-axles 14. This system is excited into torsional vibrations by the pulses from the tooth engagement between the spur bevel gear and the driving pinion 11, which under certain circumstances produce together with a natural frequency of the drive connection a disturbing resonance range.

In order to displace this natural frequency into a range where it no longer disturbs or interferes, a mass ring 15 is clamped on the synchronizing joints in a manner to be more fully described hereinafter. This takes place on that joint part which is connected directly with the output of the differential gear. In this manner, the mass of this joint member is enlarged to such an extent that the natural frequency is displaced out of the disturbing range.

According to FIG. 2, this additional ring is formed of two half-shells 15 which are connected with one another secured to one another at their two ends, for example, by means of screws or bolts 16. The arrangement is thereby made in such a manner that in the securely clamped-on position a slight clearance or play remains between the end faces 19 of the two half-shells 15. The inner surfaces 17 of the two half-shells 15 are so formed that during the clamping together, they come securely into abutment at the joint part connected with the output of the differential gear. A rubber layer 18 is arranged within the sector between the two abutment surfaces 17 which in the illustrated unstressed position has a certain oversize, i.e., projects therefore beyond the inner surfaces 17. This rubber layer 18 can be adhesively connected with the half-shells 15 or may be secured thereon in any other known manner. When clamping together the two half-shells 15, these rubber layers 18 are now pressed apart so that they abut at the joint member under a certain contract or surface pressure and produce with respect thereto a type of adhesive action, so to speak of, as a result of which a displacement of the half-shells 15 in the axial or in the circumferential direction is prevented with certainty. In order to facilitate this pressing apart of the rubber layers 18, the inner surfaces of the half-shells 15 are provided at the ends of the rubber layers 18 with corresponding bevelled or chamfered surfaces 20.

While we have shown and described only one embodiment in accordance with the present invention, it is understood that the same is not limited thereto but is susceptible of numerous changes and modifications as known to those skilled in the art, and we therefore do not wish to be limited to the details shown and described herein but intend to cover all such changes and modifications as are encompassed by the scope of the appended claims.

We claim:

1. Apparatus for the vibration damping of a drive axle means, said drive axle means comprising a differential gear means engaging and synchronized with two half-axle means by way of two synchronizing joint means symmetrically disposed with respect to said differential gear means, characterized in that rotary mass means are provided for damping the resonant frequency of the drive axle means, said rotary mass means comprising two mass ring means with each of said mass ring means being clamped to a synchronizing joint means whereby said rotary mass ring means are symmetrically disposed with respect to said differential gear means.

2. Rotary mass ring means according to claim 1, wherein the rotary mass ring means comprise two releasably connected half shell means.

3. Rotary mass ring means according to claim 1 or 2, wherein an inner surface of said rotary mass ring means is provided with an adhesive layer.

4. Rotary mass ring means according to claim 2, wherein said half shell means are substantially equal in size.

5. Rotary mass ring means according to claim 3, wherein the adhesive layer is rubber.

* * * * *